United States Patent

Kametani et al.

[11] 4,169,208
[45] Sep. 25, 1979

[54] PROCESS FOR PRODUCING UNSATURATED QUATERNARY AMMONIUM SALT

[75] Inventors: Yoshiya Kametani; Yasuo Iino, both of Yokohama, Japan

[73] Assignee: Nitto Chemical Industry Co. Ltd., Tokyo, Japan

[21] Appl. No.: 770,571

[22] Filed: Feb. 22, 1977

[51] Int. Cl.² ............................................. C07C 69/54
[52] U.S. Cl. ................................................. 560/222
[58] Field of Search ..................... 260/486 R; 560/222

[56] References Cited

U.S. PATENT DOCUMENTS 3,759,982  9/1973  Samour ................................. 560/222

Primary Examiner—Paul J. Killos
Attorney, Agent, or Firm—Cushman, Darby & Cushman

[57] ABSTRACT

An unsaturated quaternary ammonium salt represented by the formula

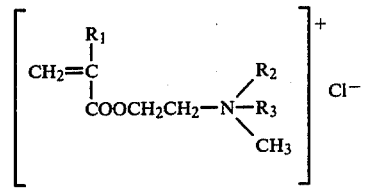

wherein $R_1$ is hydrogen atom or methyl group and $R_2$ and $R_3$ each are methyl or ethyl group, is obtained in high-quality crystalline form in a good yield by reacting an unsaturated tertiary amine repesented by the formula

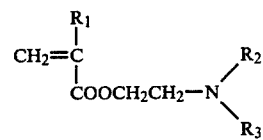

wherein $R_1$, $R_2$ and $R_3$ have the same meanings as defined above, with methyl chloride in the presence of acetonitrile used as reaction solvent. The unsaturated quaternary ammonium salt thus obtained is a substance useful as starting material in the production of flocculants, antistatics, soil conditioners, etc.

1 Claim, No Drawings

PROCESS FOR PRODUCING UNSATURATED QUATERNARY AMMONIUM SALT

This invention relates to a process for producing an unsaturated quaternary ammonium salt (II) represented by the formula

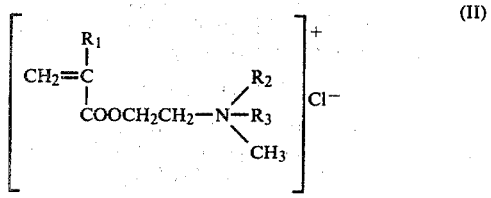

wherein $R_1$ represents hydrogen atom or methyl group and $R_2$ and $R_3$ each represent methyl or ethyl group, by reacting an unsaturated tertiary amine (I) represented by the formula

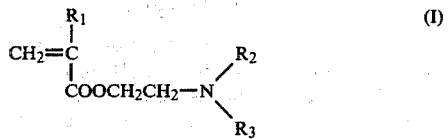

wherein $R_1$, $R_2$ and $R_3$ have the same meanings as defined above, with methyl chloride in the presence of a specified solvent, whereby said amine is quaternized and the resulting quaternary salt deposits in high-quality crystalline form in high yields.

The unsaturated quaternary ammonium salt prepared according to this invention is a monomer valuable as major starting material in the production of cationic polymers for use as flocculants, antistatics, soil conditioners, etc.

In the production of a quaternary ammonium salt by quaternizing a tertiary amine with an alkylating agent, it has heretofore been considered advantageous in view of the reaction rate to carry out this reaction in the presence of a highly polar liquid such as, for example, water, an alcohol, or the like.

However, because of a high solubility in a highly polar solvent, the unsaturated quaternary ammonium salt (II) remains dissolved in the reaction medium when prepared by the reaction of an unsaturated tertiary amine (I) and methyl chloride in the presence of water, an alcohol, or the like. Consequently, in order to obtain a crystalline unsaturated quaternary ammonium salt (II), it is necessary to remove the solvent from the reaction mixture by troublesome distillation. In addition, the crystals left behind after removal of the solvent are in the form of fine powder which is not rated as highgrade one.

On the other hand, a solid unsaturated quaternary ammonium salt (II) is obtained as a precipitate from the reaction mixture when an unsaturated tertiary amine (I) and methyl chloride are reacted in a nonpolar solvent such as, for example, a hydrocarbon in which the unsaturated quaternary ammonium salt (II) is sparingly soluble. Although this method has an advantage of simplified operation because no aftertreatment such as distillation is necessary, yet the reaction rate is slow as compared with the use of a polar solvent and the solid product obtained is not only in the form of an oil which presents difficulties in handling, for example, in removal of the solvent by filtration, but also not of a sufficient purity, containing impurities such as unreacted materials and the residual solvent.

Further, it has heretofore been proposed to employ a polar solvent such as a ketone and the like in quaternizing a tertiary amine. However, if the aforesaid unsaturated tertiary amine (I) and methyl chloride are reacted in such a solvent, it is impossible to obtain a crystalline unsaturated quaternary ammonium salt (II) in high yields and, moreover, the deposited crystals are not desirable ones because of their tendency to stick together. For instance, U.S. Pat. No. 3,948,979 has disclosed a process for synthesizing crystalline 2-methacryloxyethyltrimethyl ammonium chloride, which comprises reacting dimethylaminoethyl methacrylate and methyl chloride in a ketone such as acetone or methyl ethyl ketone or a hydrocarbon such as hexane, heptane, or benzene, used as reaction solvent. However, as described in the said patent specification, crystals of a high quality cannot be obtained unless the crude crystals separated from the reaction mixture are washed repeatedly with fresh portions of the same solvent as employed in the reaction.

Under the circumstances, the present inventors conducted various studies to find a solvent which, when used as reaction medium in preparing a crystalline unsaturated quaternary ammonium salt (II) by the reaction between an unsaturated tertiary amine (I) and methyl chloride, will yield a crystalline product that is neither oily nor required to be repeatedly washed with the solvent. As a result, it was found that acetonitrile is a solvent suitable for the purpose. Based on this finding, the present invention has been accomplished.

According to this invention, there is provided a process for producing an unsaturated quaternary ammonium salt (II) represented by the formula

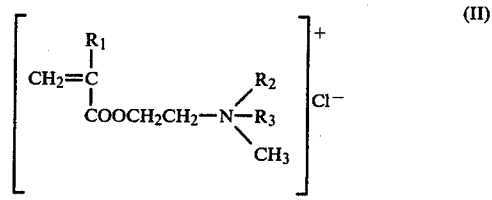

wherein $R_1$ represents hydrogen atom or methyl group and $R_2$ and $R_3$ each are methyl or ethyl group, which comprises reacting an unsaturated tertiary amine (I) represented by the formula

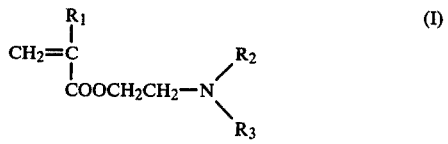

wherein $R_1$, $R_2$ and $R_3$ have the same meanings as defined above, with methyl chloride in the presence of acetonitrile to deposit said unsaturated quaternary ammonium salt in the form of high-quality crystals and in a high yield.

The unsaturated tertiary amines (I) used in this invention include dimethylaminoethyl acrylate, dimethylaminoethyl methacrylate, diethylaminoethyl acrylate, and diethylaminoethyl methacrylate.

According to this invention, the unsaturated tertiary amine (I) is reacted with methyl chloride in the presence of acetonitrile used as reaction medium. Acetonitrile is inactive to the reaction between the unsaturated tertiary amine (I) and methyl chloride. It dissolves easily both reactants, but scarcely the intended product unsaturated quaternary ammonium salt (II). Accordingly, when the tertiary amine (I) is reacted with methyl chloride in acetonitrile as reaction solvent, the reaction is unaffected by the presence of acetonitrile and a crystalline unsaturated quaternary ammonium salt deposits directly from the reaction medium. The separated crystals, moreover, were found, to the satisfaction of the present inventors, to be easily handled, being not oily, and of high quality, being free from unreacted materials and the solvent. The yield was sufficiently high. Further, on account of a sufficient volatility and not too high a boiling point (82° C.), the acetonitrile remained absorbed by the unsaturated quaternary ammonium salt crystals after filtration can be easily removed by, for example, simple heating of the recovered crystals.

In carrying out the present process, the unsaturated tertiary amine (I) and methyl chloride are used in stoichiometric ratio or methyl chloride is used in excess. It is preferable to use 1 to 2 moles of methyl chloride for 1 mole of the unsaturated tertiary amine (I). Although the amount used of the solvent is not critical, it is generally desirable in view of the convenient handling of the reaction mixture to use at least 200 ml of the solvent for 1 mole of the unsaturated tertiary amine (I).

The reaction proceeds even at room temperature. However, for the purpose of increasing the reaction rate, it is preferred to carry out the reaction at a temperature above room temperature, generally up to 100° C., preferably up to 80° C.

Since methyl chloride is a gas at room temperature, it is generally desirable to conduct the reaction by slowly introducing gaseous methyl chloride into a reactor which already contains the unsaturated tertiary amine (I), solvent, and a small amount of a polymerization inhibitor. The inhibitors include hydroquinone, hydroquinone monomethyl ether, cupferron, and phenothiazine and are used in suitable amounts to keep the monomeric components (the amine used as starting material and the quaternary ammonium salt formed) from polymerization.

The reaction time is generally in the range of several hours depending on the reaction temperature, feeding rate of methyl chloride, and the efficiency of gas-liquid contact. After the feeding of methyl chloride has been finished, if necessary, the reaction system is suitably aged to complete the reaction. The reaction mixture is then filtered to separate the deposited crystals. The crystals are then heated under atmospheric or subatmospheric pressure to remove the residual solvent and other volatiles.

The invention is further illustrated below with reference to Examples. Examples 1 to 3 pertain to the present process and Comparative Example to the conventional process.

EXAMPLE 1

Into a 1-liter reactor provided with a reflux condenser, stirrer, thermometer, and gas inlet, and kept from access of the atmospheric moisture, were charged 157 g (1 mole) of dimethylaminoethyl methacrylate, 400 ml of acetonitrile, and 0.7 g of hydroquinone monomethyl ether. Into the vigorously stirred liquid phase in the reactor, while being externally heated at 55° C., was introduced 78 g (1.5 moles) of methyl chloride over a period of 6 hours to allow the reaction to proceed. With the progress of the reaction, the amount of deposited crystals increased. After completion of the feeding of methyl chloride, the reaction mixture was cooled to room temperature and filtered to separate the crystals. The crystals separated from the reaction mixture was heated at 50° C. under reduced pressure to remove the residual solvent and other volatiles.

The colorless needle crystals thus obtained were non-sticky and were easy to handle. The crystals obtained in a yield of 95% (197.1 g) were identified as $CH_2=C.CH_3COO(CH_2)_2N(CH_3)_3.Cl$ on analysis by infrared absorption spectroscopy.

EXAMPLE 2

Into a reactor similar to that used in Example 1, were charged 143 g (1 mole) of dimethylaminoethyl acrylate, 400 ml of acetonitrile, and 0.72 g of hydroquinone monomethyl ether. From then on, the procedure of Example 1 was followed to obtain crystals of an unsaturated quaternary ammonium salt which were of the quality perfectly comparable to that of the crystals obtained in Example 1. The yield of crystals was 94% (181.9 g).

EXAMPLE 3

Into a reactor similar to that used in Example 1, were charged 185 g (1 mole) of diethylaminoethyl methacrylate, 400 ml of acetonitrile, and 0.93 g of hydroquinone. From then on, the procedure of Example 1 was followed to obtain crystals of an unsaturated quaternary ammonium salt of the quality perfectly comparable to that of the crystals obtained in Example 1. The yield was 92% (212.5 g).

COMPARATIVE EXAMPLE

Dimethylaminoethyl methacrylate and methyl chloride were reacted in the same manner as in Example 1, except that methyl ethyl ketone, methyl isobutyl ketone, tetrahydrofuran, ethyl acetate, and trichloroethylene were used each individually in place of acetonitrile. The yields of the deposited crystals were unsatisfactory, being as low as 64, 58, 42, 35, and 20%, respectively.

What is claimed is:

1. In a process for producing an unsaturated quaternary ammonium salt represented by the formula

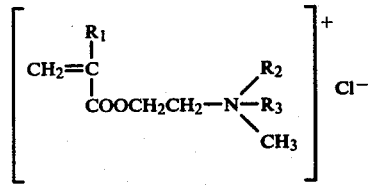

wherein $R_1$ represents hydrogen atom or methyl group and $R_2$ and $R_3$ each represent methyl or ethyl group, by reacting an unsaturated tertiary amine represented by the formula

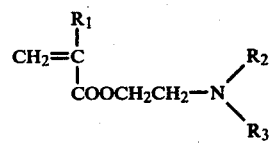

wherein $R_1$, $R_2$, and $R_3$ have the same meanings as defined above, with methyl chloride in the presence of a solvent, the improvement which comprises using acetonitrile as the solvent.

* * * * *